United States Patent
Lee

(12) 
(10) Patent No.: US 6,695,809 B1
(45) Date of Patent: Feb. 24, 2004

(54) CATHETER BALLOON WITH A DISCONTINUOUS ELASTOMERIC OUTER LAYER

(75) Inventor: Jeong S. Lee, Diamond Bar, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/394,653

(22) Filed: Sep. 13, 1999

(51) Int. Cl.[7] .......................... A61M 29/00; A61F 11/00
(52) U.S. Cl. ..................... 604/96.01; 606/108
(58) Field of Search .................. 604/96.01, 103.05, 604/103.06, 103.09, 103.11, 103.13, 103.08; 606/108, 192, 194

(56) References Cited

U.S. PATENT DOCUMENTS

| | | | |
|---|---|---|---|
| 2,927,584 A | * | 3/1960 | Wallace |
| 4,637,396 A | * | 1/1987 | Cook ......................... 604/102 |
| 4,702,252 A | | 10/1987 | Brooks et al. ............. 128/344 |
| 4,706,670 A | | 11/1987 | Anderson et al. .......... 128/344 |
| 4,921,484 A | * | 5/1990 | Hillstead .................... 604/104 |
| 5,108,416 A | | 4/1992 | Ryan et al. ................. 606/194 |
| 5,112,304 A | | 5/1992 | Barlow et al. .............. 604/96 |
| 5,250,070 A | * | 10/1993 | Parodi ........................ 606/194 |
| 5,647,848 A | | 7/1997 | Jorgensen ................... 604/96 |
| 5,720,726 A | * | 2/1998 | Marcadis et al. ........... 604/96 |
| 5,752,934 A | | 5/1998 | Campbell et al. ........... 604/96 |
| 5,879,369 A | | 3/1999 | Ishida ........................ 606/194 |
| 5,911,702 A | * | 6/1999 | Romley et al. .............. 604/53 |
| 6,010,480 A | * | 1/2000 | Abele et al. ................ 604/96 |
| 6,010,521 A | * | 1/2000 | Lee et al. ................... 606/194 |
| 6,129,706 A | * | 10/2000 | Janacek ..................... 604/96 |

* cited by examiner

Primary Examiner—Sharon Kennedy
(74) Attorney, Agent, or Firm—Fulwider Patton Lee & Utecht, LLP

(57) ABSTRACT

An intraluminal balloon catheter with an elongated shaft, and an inflatable balloon on the shaft which has an inner layer and a discontinuous outer layer formed at least in part of an elastomeric polymeric material. In a presently preferred embodiment, the catheter is a stent delivery catheter with a stent disposed on the balloon in contact with at least a section of the discontinuous outer layer of the balloon. The discontinuous outer layer of the balloon may comprise fibers or strands of the elastomeric material woven into a braided, webbed, meshed, wrapped or wound outer layer of the balloon.

17 Claims, 2 Drawing Sheets

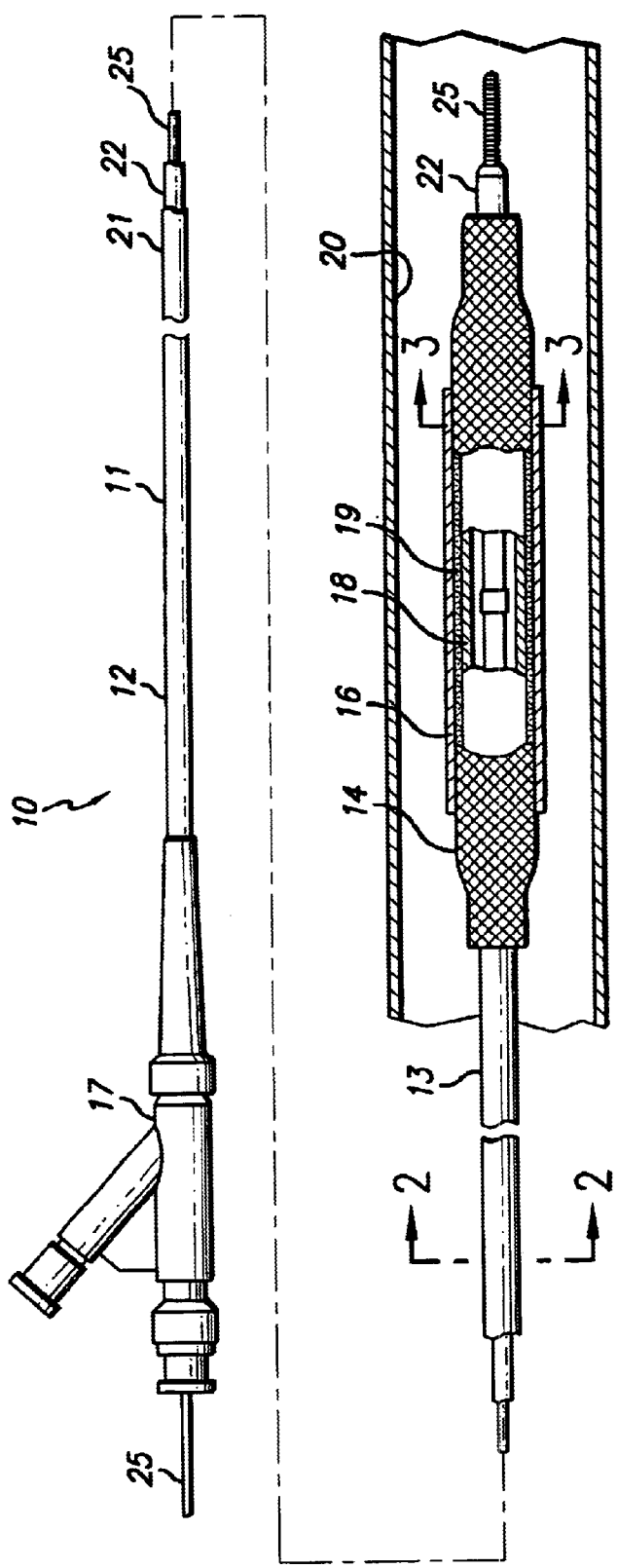
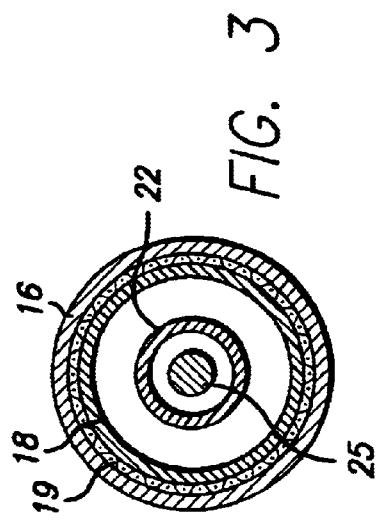
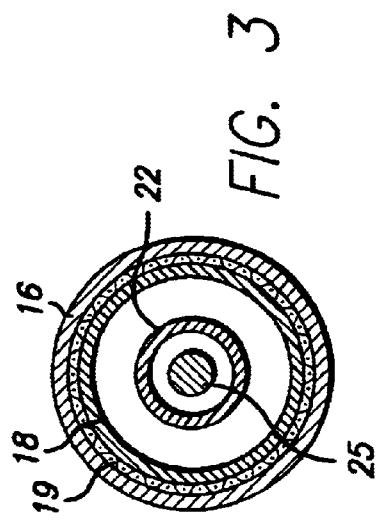

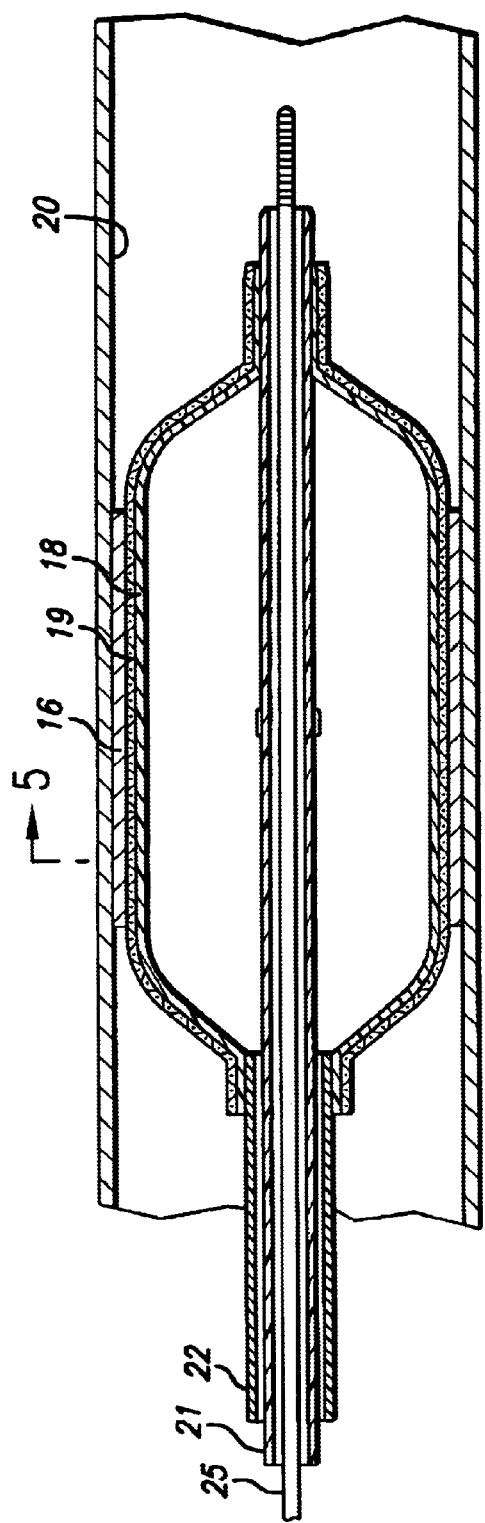
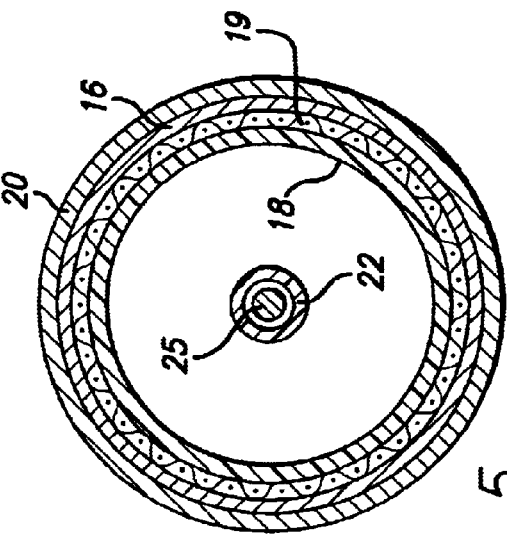
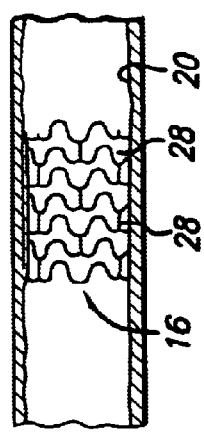
FIG. 4
FIG. 5
FIG. 6

CATHETER BALLOON WITH A DISCONTINUOUS ELASTOMERIC OUTER LAYER

BACKGROUND OF THE INVENTION

This invention generally relates to intraluminal catheters, and particularly to balloon catheters used for stent delivery and percutaneous transluminal coronary angioplasty (PTCA).

PTCA is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and thereby increase the blood flow there through. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced until the preshaped distal tip of the guiding catheter is disposed within the aorta adjacent the ostium of the desired coronary artery, and the distal tip of the guiding catheter is then maneuvered into the ostium. A balloon dilatation catheter may then be advanced through the guiding catheter into the patient's coronary artery until the balloon on the catheter is disposed within the stenotic region of the patient's artery. The balloon is inflated to open up the arterial passageway and increase the blood flow through the artery. Generally, the inflated diameter of the balloon is approximately the same diameter as the native diameter of the body lumen being dilated so as to complete the dilatation but not over expand the artery wall. After the balloon is finally deflated, blood flow resumes through the dilated artery and the dilatation catheter can be removed therefrom.

To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference in their entireties. The implantation of a stent at the site of the dilatation can significantly reduce the restenosis rate.

One difficulty has been retention of the stent on the catheter balloon. The balloon must retain the stent during advancement of the catheter within the patient's vasculature, and yet still provide for expansion and release of the stent once the balloon is positioned at the desired location. It would be a significant advance to provide a catheter balloon having improved stent retention, and without inhibiting balloon or catheter function. The present invention satisfies these and other needs.

SUMMARY OF THE INVENTION

The invention is directed to an intraluminal balloon catheter with an elongated shaft, and an inflatable balloon on the shaft which has an inner layer and a discontinuous outer layer. The discontinuous outer layer is formed at least in part of an elastomeric polymeric material. In a presently preferred embodiment, the catheter is a stent delivery catheter with a stent disposed on the balloon in contact with at least a section of the discontinuous outer layer of the balloon.

In one embodiment, the discontinuous outer layer of the balloon comprises woven fibers, or strands, of the elastomeric material. The term woven should be understood to include a variety of arrangements of fibers including a fiber braided, webbed, meshed, wrapped or wound to form the outer layer of the balloon. The fibers may be tightly or loosely woven with openings or spaces between adjacent fibers of a mesh or adjacent sections of a wound fiber of about 0.01 mm to about 0.10 mm, preferably about 0.03 mm to about 0.07 mm. Because the outer layer is discontinuous, it improves stent retention while minimizing the disadvantageous effects, such as increased bulk and stiffness, of providing a continuous outer layer on the balloon.

The outer layer of the balloon extends along at least a section of the working length of the balloon, to provide for improved stent retention thereon. In a presently preferred embodiment, the length of the outer layer is about equal to the length of the inner layer of the balloon. Alternatively, the outer layer may have a length less than the length of the inner layer of the balloon, as for example when the length of the outer layer is equal to or less than the working length of the balloon. Additionally, the outer layer of the balloon may have a length greater than the length of the inner layer of the balloon, so that the outer layer extends beyond the balloon and onto at least a section of the catheter shaft. In the embodiments in which the outer layer extends over the tapered sections of the balloon, the outer layer reduces longitudinal elongation of the balloon when it is expanded under pressure.

The elastomeric outer layer of the balloon is preferably formed of thermoplastic elastomers, including polyesters such as HYTREL or LOMOD, polyamides, polyether block amides such as PEBAX, polyurethane and polyurethane block copolymers such as PELLETHANE. In a presently preferred embodiment, the thermoplastic elastomer is in the same family of materials as the material used to form the inner layer of the balloon, so that the materials are compatible and, consequently, heat fusible together. The elastomeric material provides an outer layer which is somewhat tacky. Consequently, the outer layer improves stent retention on the balloon by frictionally engaging the stent.

The inner layer of the balloon may be formed of a variety of polymeric materials used for forming catheter balloons. The inner layer is preferably formed of a polymeric material which produces a noncompliant or semicompliant inner layer to provide controlled expansion. However, a compliant inner layer may also be used. The compliance of a balloon is a measure of the ease with which a balloon expands under pressure. Noncompliant and semicompliant balloons require relatively higher pressures to expand than do compliant balloons formed from materials such as elastomers. Typically, noncompliant balloons have a compliance of less than about 0.025 mm/atm, semicompliant balloons have a compliance of about 0.025 to about 0.045 mm/atm, and compliant balloons have a compliance of greater than about 0.045 mm/atm. In a presently preferred embodiment, the inner layer is formed of high molecular weight orientable semicrystalline materials such as polyolefin, polyethyleneterephthalate (PET), nylon, polybutyleneterephthalate (PBT), polyethylene napthalate (PEN), and polyetheretherketone (PEEK), providing a noncompliant or semicompliant balloon. In a presently preferred embodiment, the inner layer of the balloon is a single polymeric layer. However, the inner layer may also be multilayered, as for example where the inner layer is formed by coextruding two or more layers of different polymeric materials.

Various designs for balloon catheters well known in the art may be used in the catheter of the invention. For example, the catheter may be a conventional over-the-wire dilatation catheter for angioplasty or stent delivery having a guidewire receiving lumen extending the length of the catheter shaft from a guidewire port in the proximal end of the shaft, or a rapid exchange catheter having a short guidewire lumen extending to the distal end of the shaft from a guidewire port located distal to the proximal end of the shaft.

The catheter balloon of the invention has excellent stent retention due to the outer layer of elastomeric polymeric material. The discontinuous elastomeric outer layer provides for frictional retention of a stent without disadvantageously effecting the ability of the balloon to expand and release the stent within a patient's body lumen. The embodiment having a semicompliant or noncompliant inner layer provides a balloon having controlled expansion. These and other advantages of the invention will become more apparent from the following detailed description of the invention and the accompanying exemplary drawings.

BRIEF DESCRIPTION OF THE DRAWINGS

FIG. 1 is an elevational view, partially in section, of a catheter which embodies features of the invention, showing the balloon in an unexpanded state within a patient's body lumen.

FIG. 2 is a transverse cross sectional view of the catheter of FIG. 1 taken along lines 2—2.

FIG. 3 is a transverse cross sectional view of the catheter of FIG. 1 taken along lines 3—3.

FIG. 4 is a longitudinal cross sectional view of the catheter of FIG. 1, showing the balloon in an expanded state within the body lumen.

FIG. 5 is a transverse cross sectional view of the catheter of FIG. 4 taken along lines 5—5.

FIG. 6 illustrates an open-walled stent after being implanted in the body lumen.

DETAILED DESCRIPTION OF THE INVENTION

As shown in FIG. 1, a catheter 10 embodying features of the invention generally includes an elongated catheter shaft 11 having a proximal section 12, a distal section 13, an inflatable balloon 14 on the distal section 13 of the catheter shaft 11, and an adapter 17 mounted on the proximal section 12 of shaft 11 to direct inflation fluid to the interior of the inflatable balloon. The balloon 14 has an inner layer 18, and a discontinuous outer layer 19 formed at least in part of an elastomeric material. In the embodiment illustrated in FIG. 1, the outer layer has a length equal to the length of the inner layer.

In the embodiment illustrated in FIG. 1, the intravascular catheter 10 is an over-the-wire catheter, and is illustrated within a patient's body lumen 20 with the balloon 14 in an unexpanded state. The catheter shaft 11 has an outer tubular member 21 and an inner tubular member 22 disposed within the outer tubular member and defining, with the outer tubular member, inflation lumen 23. Inflation lumen 23 is in fluid communication with the interior chamber 15 of the inflatable balloon 14. The inner tubular member 22 has an inner lumen 24 extending therein, which is configured to slidably receive a guidewire 25 suitable for advancement through a patient's coronary arteries. The distal extremity of the inflatable balloon 14 is sealingly secured to the distal extremity of the inner tubular member 22 and the proximal extremity of the balloon is sealingly secured to the distal extremity of the outer tubular member 21. FIGS. 2 and 3, showing a transverse cross section of the catheter, illustrate the guidewire receiving lumen 24, inflation lumen 23, and balloon interior. The balloon 14 can be inflated by radiopaque fluid from an inflation port 26 through inflation lumen 23 contained in the catheter shaft 11. The details and mechanics of balloon inflation vary according to the specific design of the catheter, and are well known in the art.

In the embodiment illustrated in FIG. 1, the discontinuous outer layer 19 comprises woven fibers 26 of elastomeric material forming a mesh having openings 27 between adjacent fibers. The fibers 26 have a transverse dimension, i.e., width, of about 0.01 mm to about 0.10 mm, and preferably at least about 0.03 mm. The dimensions of the openings 27 between the adjacent fibers 26 of the open-walled mesh may vary. Preferably, the openings 27 are about 0.25 mm to about 2.0 mm, preferably about 0.50 mm to about 1.0 mm in length, or about 2000% to about 4000% of the transverse dimension of the fiber 26. In a presently preferred embodiment, the openings 27 between the adjacent fibers 26 of the discontinuous outer layer 19 have a length which is not greater than the length of the openings in the wall of the stent 1 6 mounted on the balloon 14, to thereby provide improved contact between the stent and the discontinuous outer layer 19. FIG. 6 illustrates open-walled stent 16, with openings 28 in a wall of the stent, after being implanted in the body lumen 20.

The outer layer 19 is preferably bonded to the inner layer 18, as for example by a heat fusion bond or an adhesive bond. In a presently preferred embodiment, the inner layer 18 is expanded to form the balloon 14 before the outer layer 19 is applied thereto. The balloon 14 is inflated with elevated pressure, and the elastomeric fibers 26 are wound or braided onto the balloon 14 and bonded to the inner layer 18 by heat fusing or adhesive bonding. Alternatively, the balloon 14 is formed by winding or braiding elastomeric fibers 26 onto a parison comprising an extruded tube of the inner layer polymeric material. The parison with the elastomeric fibers thereon is then expanded to form the balloon, as for example by blow molding at elevated temperature and pressure. In this embodiment, a separate step of heat fusing or adhesive bonding the outer layer to the inner layer is not required if the inner and outer layers are formed of compatible materials which therefore fusion bond during the blow molding.

The presently preferred thermoplastic elastomeric material for the outer layer 19 is Pebax 40D. The outer layer elastomeric polymeric material has an elongation at break at about room temperature of at least about 200%, preferably about 300% to about 600%, and a tensile strength at break of at least about 4000 psi (28 MPa), and preferably about 4,500 psi (32 MPa) to about 7,300 psi (51 MPa). The polymeric material for the inner layer 18 of the balloon is preferably a high molecular weight orientable semicrystalline polymer. The presently preferred material for the inner layer 18 is Pebax 72D or Nylon 12. The inner layer polymeric material has an elongation at break at about room temperature of at least about 200%, preferably about 250% to about 400%, and a tensile strength at break of at least about 7,000 psi (50 MPa), and preferably about 7,500 psi (53 MPa) to about 10,000 psi (70 MPa). The inner layer 18 is preferably noncompliant or semicompliant, so that the balloon would typically be folded into a low profile configuration having wings (not shown) for advancement within the patient's vasculature.

To the extent not previously discussed herein, the balloon 14 of the invention can be produced by conventional techniques for producing catheter inflatable members, such as blow molding, and may be preformed by stretching a straight tube, at elevated temperatures, before the balloon is blown. The balloons may be formed by expansion of tubing, as for example at a hoop ratio of between about 3 and about 8. The bonding of the balloon to the catheter may be by conventional techniques, such as adhesives and fusion with compatibilizers, as for example are described in U.S. Pat. No. 5,074,845 (Miraki et al.), incorporated by reference.

The length of the balloon 14 may be about 0.5 cm to about 6 cm, preferably about 1.0 cm to about 4.0 cm. After being formed, the outer diameter of the balloon at nominal pressure (e.g. 6–8 ATM) is generally about 1 mm to about 4 mm, and typically about 3 mm, although balloons having an outer diameter of about 1 cm may also be used. The inner layer single wall thickness is about 0.0005 inches (0.013 mm) to about 0.001 inches (0.025 mm), and the single wall thickness of the outer layer is about 0.0007 inches (0.02 mm) to about 0.002 inches (0.05 mm).

In the embodiment of the invention shown in FIG. 1, a stent 16 is disposed about the balloon 14 for delivery within patient's vessel. The stent 16 may be any of a variety of stent materials and forms designed to be implanted by an expanding member, see for example U.S. Pat. No. 5,514,154 (Lau et al.) and U.S. Pat. No. 5,443,500 (Sigwart), previously incorporated herein by reference. For example, the stent material may be stainless steel, a NiTi alloy or various other materials. The stent 16 is shown in an unexpanded state in FIG. 1. The stent 16 has a smaller diameter for insertion and advancement into the patient's lumen, and is expandable to a larger diameter for implanting in the patient's vessel. FIG. 4 illustrates the balloon 14 and stent 16 thereon expanded within the body lumen 20. FIG. 5 illustrates a transverse cross section of the catheter shown in FIG. 4, taken along lines 5—5. After expansion of the stent 16 within the body lumen 20, the balloon 14 is deflated and withdrawn from the body lumen, leaving the expanded stent implanted therein.

It will be apparent from the foregoing that, while particular forms of the invention have been illustrated and described, various modifications can be made without departing from the spirit and scope of the invention. For example, while the balloon catheter illustrated in FIG. 1 has inner and outer tubular members with independent lumens, a single tubular membered shaft having two lumens therein may also be used. Other modifications may be made without departing from the scope of the invention.

What is claimed is:

1. A balloon catheter, comprising:
    a) an elongated shaft having a proximal end, a distal end, and at least one lumen extending therein; and
    b) a balloon inflatable from an unexpanded configuration to an expanded configuration and a having a continuous inner layer configured to retain inflation fluid, and a discontinuous outermost layer bonded to an outer surface of the inner layer and extending about an entire circumference of said inner layer and longitudinally along at least a section of the inner layer and formed at least in part of a woven elastomeric polymeric material.

2. The balloon catheter of claim 1, wherein the woven elastomeric polymeric material comprises fibers having a transverse dimension of at least about 0.2 mm.

3. The balloon catheter of claim 1, wherein the woven elastomeric polymeric material comprises fibers having a dimension of about 0.02 mm to about 0.05 mm.

4. The balloon catheter of claim 1, wherein the woven elastomeric polymeric material comprises fibers and forms a mesh having openings between adjacent fibers.

5. The balloon catheter of claim 4 wherein the openings are about 0.25 to about 2.0 mm in length.

6. The balloon catheter of claim 1 wherein the discontinuous outer layer extends at least over a working length of the balloon.

7. The balloon catheter of claim 1 wherein the discontinuous outer layer of the balloon has a length about equal to a length of the inner layer of the balloon.

8. The balloon catheter of claim 1 wherein in the elastomeric polymeric material is a thermoplastic elastomer selected from the group consisting of polyester, polyamide, polyether block amide, and polyurethane.

9. The balloon catheter of claim 1 wherein the inner layer is formed of a polymeric material.

10. The balloon catheter of claim 9 wherein the inner layer polymeric material forms a semicompliant or a noncompliant inner layer.

11. The balloon catheter of claim 10 wherein the inner layer polymeric material comprises a high molecular weight, orientable, semicrystalline polymer.

12. The balloon catheter of claim 10 wherein the inner layer polymeric material is selected from the group consisting of polyolefin, polyethyleneterephthalate, nylon, polybutyleneterephthalate, PEN, polyetherether ketone, and polyurethane.

13. The balloon catheter of claim 9 wherein the inner layer polymeric material is compatible with the outer layer elastomeric polymeric material.

14. The balloon catheter of claim 13 wherein the inner layer polymeric material comprises a polyamide and the outer layer elastomeric polymeric material comprises polyether block amide.

15. A stent delivery catheter, comprising:
    a) an elongated shaft having a proximal end, a distal end, and inflation lumen extending within at least a portion of a distal shaft section to a location spaced proximally from the distal end;
    b) an inflatable balloon on the distal shaft section being inflatable from an unexpanded configuration to an expanded configuration and having an inner layer and a discontinuous outer layer, said discontinuous outer layer being formed at least in part of an elastomeric polymeric material, said discontinuous outer layer extending around an entire circumference of at least a section of the balloon; and
    c) a stent disposed about said balloon, said stent having an inner surface in contact with said discontinuous layer, said stent contacting said discontinuous outer layer around an entire circumference of at least a section of the stent, said contacting occurring when said balloon is in the unexpanded and expanded configurations.

16. The stent delivery catheter of claim 15 wherein the discontinuous outer layer comprises woven fibers of the elastomeric polymeric material.

17. The stent delivery catheter of claim 16 wherein the woven fibers form a mesh having openings between adjacent fibers, and the stent comprises an open-walled structure, the mesh openings having a length not greater than openings in a wall of the stent.

* * * * *